(12) United States Patent
Sasane et al.

(10) Patent No.: US 10,479,776 B2
(45) Date of Patent: Nov. 19, 2019

(54) PROCESS FOR THE PREPARATION OF EFINACONAZOLE

(71) Applicant: LUPIN LIMITED, Mumbai (IN)

(72) Inventors: Sachin Arun Sasane, Maharashtra (IN); Devendrakumar Paramsukh Varma, Maharashtra (IN); Rajesh Harishankar Vyas, Maharashtra (IN); Nandu Baban Bhise, Maharashtra (IN); Girij Pal Singh, Maharashtra (IN); Krishnat Hanmant Kumbhar, Maharashtra (IN)

(73) Assignee: LUPIN LIMITED, Mumbai (IN)

( * ) Notice: Subject to any disclaimer, the term of this patent is extended or adjusted under 35 U.S.C. 154(b) by 0 days.

(21) Appl. No.: 15/573,082

(22) PCT Filed: May 10, 2016

(86) PCT No.: PCT/IB2016/052667
§ 371 (c)(1),
(2) Date: Nov. 9, 2017

(87) PCT Pub. No.: WO2016/181306
PCT Pub. Date: Nov. 17, 2016

(65) Prior Publication Data
US 2018/0118714 A1    May 3, 2018

(30) Foreign Application Priority Data
May 12, 2015  (IN) .......................... 1875/MUM/2015

(51) Int. Cl.
*C07D 401/06* (2006.01)
(52) U.S. Cl.
CPC ........ *C07D 401/06* (2013.01); *C07B 2200/13* (2013.01)

(58) Field of Classification Search
None
See application file for complete search history.

(56) References Cited

U.S. PATENT DOCUMENTS 5,620,994 A    4/1997  Naito et al.
8,871,942 B2   10/2014 Mimura et al.

FOREIGN PATENT DOCUMENTS

EP    0698606 A1    2/1996

OTHER PUBLICATIONS

Ogura, H. et al., Chem. Pharm Bull. 1999 vol. 47, pp. 1417-1425.*
International Search Report and Written Opinion from International Application No. PCT/IB2016/052667, dated Sep. 12, 2016.
Ogura, H. et al.: "Synthesis and Antifungal Activities of (2R,3R)-2-Aryl-1-azolyl-3(substituted amino)-2-butanol Derivatives as Topical Antifungal Agents", Chem. Pharm. Bull., vol. 47, 1999, pp. 1417-1425, XP002759239.
Ogura, H., "Synthesis and Antifungal Activities of (2R,3R)-2-Aryl-1-azolyl-3-(substituted amino)-2-butanol Derivatives as Topical Antifungal Agents," Chem. Pharm. Bull. 47(10), 1417-1425 (Oct. 1999).

* cited by examiner

*Primary Examiner* — Heidi Reese
(74) *Attorney, Agent, or Firm* — Merchant & Gould P.C.

(57) ABSTRACT

The present invention provides an improved process for the preparation of Efinaconazole in higher yield by the ring-opening addition reaction of epoxytriazole with 4-methylenepiperidine or its acid addition salt under mild conditions without using a large excess of 4-methylenepiperidine in the presence of an alkali or an alkaline earth metal halide.

3 Claims, 1 Drawing Sheet

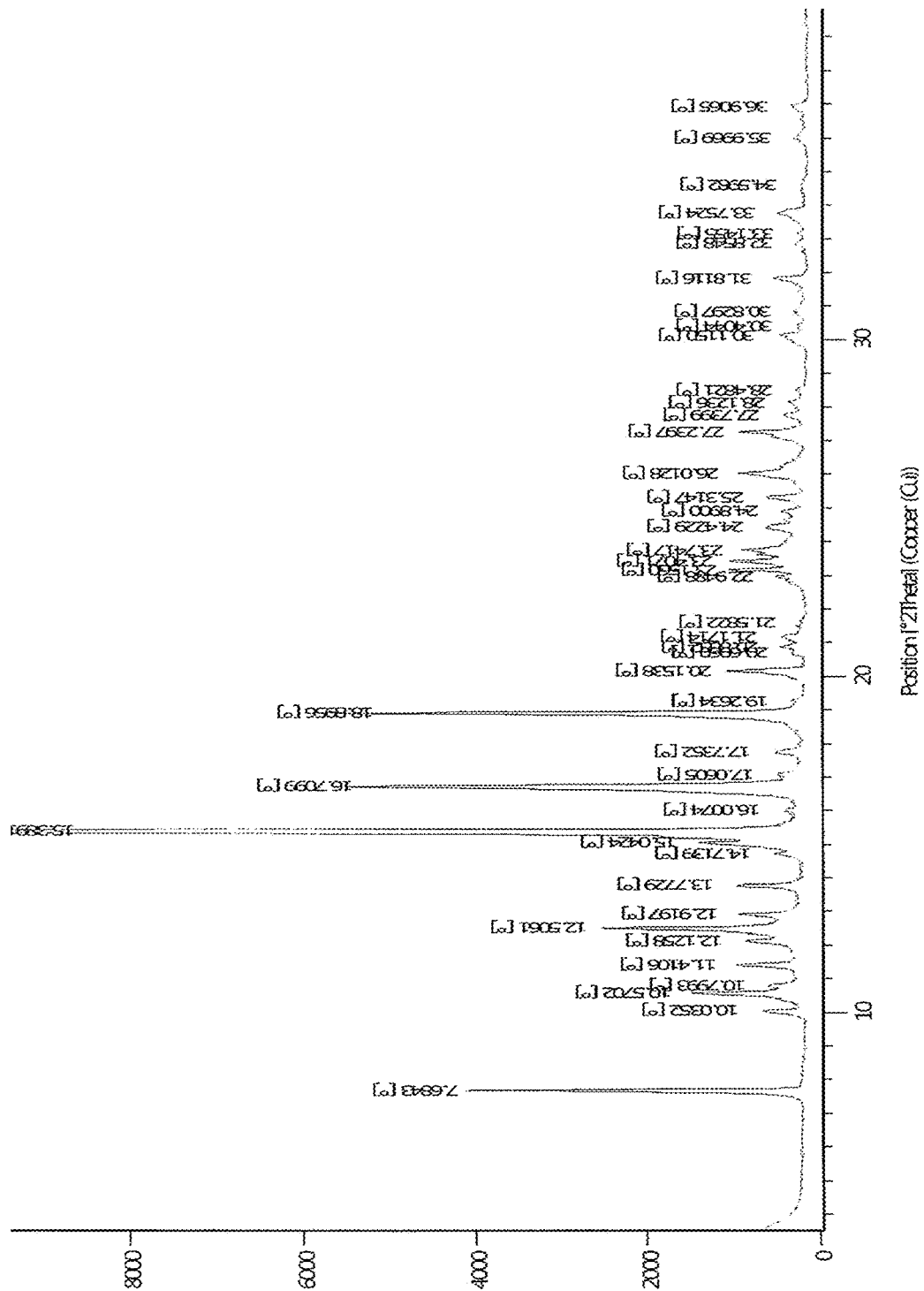

PROCESS FOR THE PREPARATION OF EFINACONAZOLE

This application is a National Stage Application of PCT/IB2016/052667, filed 10 May 2016, which claims benefit of Serial No. 1875/MUM/2015, filed 12 May 2015 in India and which applications are incorporated herein by reference. To the extent appropriate, a claim of priority is made to each of the above disclosed applications.

TECHNICAL FIELD OF INVENTION

The present invention is relates to an improved process for the preparation of (2R,3R)-2-(2,4-difluorophenyl)-3-(4-methylenepiperidin-1-yl)-1-(1H-1,2,4-triazol-1-yl)butan-2-ol (Efinaconazole).

BACKGROUND OF THE INVENTION

Efinaconazole, (2R,3R)-2-(2,4-difluorophenyl)-3-(4-methylenepiperidin-1-yl)-1-(1H-1,2,4-triazol-1-yl)butan-2-ol, also known as KP-103 and marketed under the trade name JUBLIA®' is effective against mycotic diseases in humans and animals represented by formula I:

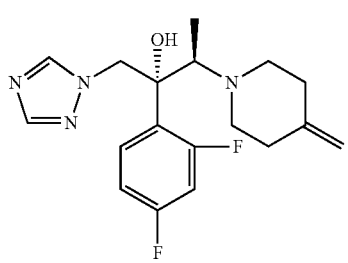

Formula 1

U.S. Pat. No. 5,620,994 describe azolylamine derivatives and their use including Efinaconazole or pharmaceutically acceptable acid addition salts thereof, a pharmaceutical composition and a method of use.

The U.S. Pat. No. '994 also discloses a process for the preparation of Efinaconazole by reaction of (2R,3S)-2-(2,4-difluorophenyl)-3-methyl-2-[(1H-1,2,4-triazol-1-yl)methyl]oxirane (Formula 2) with 4-methylenepiperidine. In this method, the ring-opening addition reaction uses a large excess of 4-methylenepiperidine in water and involves prolonged heating under reflux.

U.S. Pat. No. 8,871,942 describes a process for the preparation of Efinaconazole. In this Efinaconazole obtained by reaction of (2R,3S)-2-(2,4-difluorophenyl)-3-methyl-2-[(1H-1,2,4-triazol-1-yl)methyl]oxirane (Formula 2) with acid addition salt of 4-methylenepiperidine.

There is always a need for alternative preparative routes, which for example, use reagents, solvents that are less expensive, and/or easier to handle, consume smaller amounts of reagents and solvents, provide a higher yield of product, involve fewer steps, have smaller and/or more eco-friendly waste products, and/or provide a product of higher purity.

DESCRIPTION OF DRAWINGS

FIG. 1: illustrates X-ray powder diffraction pattern of crystalline form L1 of Efinaconazole.

SUMMARY OF THE INVENTION

In one aspect, the present invention relates to a process for the preparation of Efinaconazole of formula 1 comprises reacting (2R,3S)-2-(2,4-difluorophenyl)-3-methyl-2-[(1H-1,2,4-triazol-1-yl)methyl]oxirane (Formula 2) with 4-methylenepiperidine or its acid addition salt in the presence of an alkali or an alkaline earth metal halide.

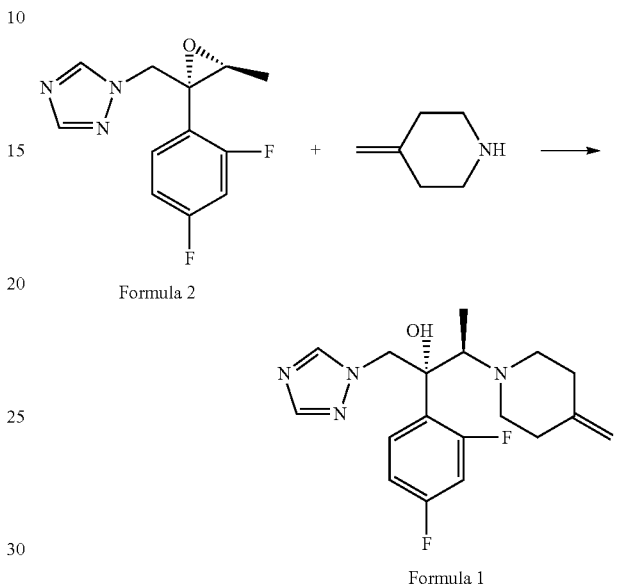

Formula 2

Formula 1

In another aspect, the present invention relates to novel crystalline forms of Efinaconazole and process for the preparation thereof.

In another aspect, the present invention relates to is a pharmaceutical composition comprising said novel crystalline forms of Efinaconazole and one or more pharmaceutically acceptable excipients.

DESCRIPTION OF THE INVENTION

Unless otherwise indicated, the following definitions are set forth to illustrate and define the meaning and scope of the various terms used to describe the invention herein.

As used herein, the term "pharmaceutical composition" refers to a mixture containing a pharmaceutically active ingredient, such as efinaconazole, and one or more pharmaceutically acceptable excipients (antioxidants, preservatives, carriers, etc.). Compositions for topical administration are formulated as solutions, sprays, ointments, lotions, gels, shampoos, and the like. "Pharmaceutically acceptable" compositions are those in which substituent components such as carriers, diluents, and excipients are compatible with each other and with the active ingredient. Pharmaceutically acceptable compositions are frequently made with pharmaceutical-grade active agents and excipients.

As used herein, the term "acid addition salt" refers to the acid that forms the acid addition salt of 4-methylenepiperidine may basically be any acid that forms salts with amines and examples include, but are not limited to, inorganic salts such as hydrochloric acid, hydrobromic acid, hydroiodic acid, sulfuric acid, nitric acid, phosphoric acid, boric acid, chloric acid, and carbonic acid, as well as organic acids such as formic acid, acetic acid, trifluoroacetic acid, propionic acid, oxalic acid, methanesulfonic acid, benzenesulfonic acid, and p-toluenesulfonic acid. Preferred examples of the acid include hydrochloric acid, hydrobromic acid, hydroiodic acid, nitric acid, and trifluoroacetic acid, and hydrobromic acid or hydroiodic acid is more preferred.

According to one aspect, the present invention provides a process for the preparation of Efinaconazole of formula 1 comprises reacting (2R,3S)-2-(2,4-difluorophenyl)-3-methyl-2-[(1H-1,2,4-triazol-1-yl)methyl]oxirane (Formula 2) with 4-methylenepiperidine or its acid addition salt in a reaction solvent in the presence of an alkali or an alkaline earth metal halide.

Reaction solvent include but not limited to alcohols such as methanol, ethanol, isopropanol, and 1-butanol; aprotic polar solvents (esters such as ethyl acetate and butyl acetate; amides such as N,N-dimethylformamide, N,N-dimethylacetamide, and N-methylpyrrolidone; ethers such as tetrahydrofuran, 1,4-dioxane, 1,2-dimethoxyethane, and cyclopentyl methyl ether; ketones such as acetone and methyl ethyl ketone; other solvents such as acetonitrile, dimethyl sulfoxide, nitromethane, and 4-methyl-2-pentanone); mixtures of two or more of these solvents; and mixed solvents consisting of water and at least one of the above-mentioned solvents.

The above reaction can also be performed in absence of solvent under neat condition.

Examples of an alkali metal or an alkaline earth metal halide to be used in the reaction of the present invention include but not limited to lithium halide, sodium halide, potassium halide, rubidium halide, cesium halide, beryllium halide, magnesium halide, calcium halide, strontium halide and barium halide. More preferred are lithium halide, calcium halide and even more preferred are lithium halide. The halide is selected from fluoride, chloride, bromide and iodide. More preferred halides are chloride, bromide and iodide.

4-methylenepiperidine is typically used in amounts ranging from 1 to 5 equivalents to Formula 2.

The reaction is performed at temperatures in the range from 0° C. to 150° C. The reaction time varies with the reaction temperature, the solvent used, and other factors, but it typically ranges from 1 to 24 hours.

The compound obtained by the reaction may be purified in the usual manner as by recrystallization or chromatography.

According to another aspect, the present invention provides novel crystalline forms of Efinaconazole and process for preparation thereof. One of the novel polymorph of the present invention is designated as crystalline form L1, characterized by XRPD (X-ray powder diffractogram) which comprises of peaks expressed as 2Θ at 7.6, 15.3, 16.6, and 18.8±0.2 degrees.

In another aspect, the invention provides a process for preparation of novel crystalline forms of Efinaconazole comprising the steps of:
(i) providing a solution of Efinaconazole in organic solvent;
(ii) optionally cooling the above solution; and
(iii) isolating pure Efinaconazole.

In one embodiment, the organic solvent used in step-(i) is selected from water, methanol, ethanol, isopropyl alcohol, n-butanol, tert-butanol, acetone, methyl ethyl ketone, methyl isobutyl ketone, methyl tert-butyl ketone, n-heptane, cyclohexane, toluene, methylene chloride, and the like and mixtures thereof.

Step-(i) of providing a solution of Efinaconazole includes dissolving Efinaconazole in the organic solvent, or obtaining an existing solution from a previous processing step. The suitable organic solvents include, but are not limited to, water, methanol, ethanol, isopropyl alcohol, n-butanol, tert-butanol, acetone, methyl ethyl ketone, methyl isobutyl ketone, methyl tert-butyl ketone, n-heptane, cyclohexane, toluene, methylene chloride.

Efinaconazole can be dissolved in the solvent at a temperature of below about reflux temperature of the solvent used, specifically at about 35° C. to about 150° C. Cooling the solution of step-(ii) at a temperature of below 30° C.

In another embodiment, isolation of pure Efinaconazole can be carried out by conventional techniques known in the prior art such as filtration, concentration, evaporation etc.; preferably by filtration.

According to another aspect, the present invention provides use of the novel crystalline forms of Efinaconazole for the manufacture of a pharmaceutical composition together with a pharmaceutically acceptable carrier.

According to another aspect, there is provided pharmaceutical compositions comprising novel crystalline forms of efinaconazole and one or more pharmaceutically acceptable excipients.

Pharmaceutical compositions comprise at least a therapeutically effective amount of the novel crystalline forms of efinaconazole. Such pharmaceutical compositions may be administered to a mammalian patient in a dosage form, e.g., solid, liquid, solution, powder, elixir, aerosol, syrup, injectable solution, etc. Dosage forms may be adapted for administration to the patient by oral, buccal, parenteral, ophthalmic, rectal and transdermal routes or any other acceptable route of administration. Oral dosage forms include, but are not limited to, tablets, pills, capsules, syrup, troches, sachets, suspensions, powders, lozenges, elixirs and the like. The novel crystalline form of efinaconazole may also be administered as compositions for topical administration are formulated as solutions, sprays, ointments, lotions, gels, shampoos, and the like.

The pharmaceutical compositions further contain one or more pharmaceutically acceptable excipients. Suitable excipients and the amounts to use may be readily determined by the formulation scientist based upon experience and consideration of standard procedures and reference works in the field, e.g., the buffering agents, sweetening agents, binders, diluents, fillers, lubricants, wetting agents and disintegrates.

The invention is further illustrated by following examples, which should not be construed as limiting to the scope of invention.

EXAMPLES

The X-ray diffraction patterns were measured using Philips X'Pertpro machine with following measurement parameters:
Scan axis: Gonio
Step size: 0.0066°
Scan type: continuous
Divergence slit size: 0.25°
Anode material: Cu
Radiation type: K-alpha 1
Scan: 3.5 to 40° 2θ
Spinning: Yes
Measurement temperature: 25° C.

Example 1

Preparation of Efinaconazole from 4-methylene Piperidine Base and (2R,3S)-2-(2,4-difluorophenyl)-3-methyl-2-[(1H-1,2,4-triazol-1-yl)methyl]oxirane 4-methylenepiperidine (2.9 g, 0.03 mole) and lithium bromide (2.6 g, 0.03 mole) was charged to acetonitrile in a Flask. Mixture was allowed to stir and (2R,3S)-2-(2,4-difluorophenyl)-3-methyl-2-[(1H-1,2,4-triazol-1-yl)methyl]oxirane (2.5 g, 0.01 mole) was added to it. Reaction mixture was then heated at reflux temperature for 24 Hrs. to complete the reaction. Reaction mass was cooled up to room temperature followed by water and ethyl acetate mixture (1:1) was added. Reaction mixture was stirred and organic layer was separated. Organic layer was distilled out under vacuum at 45-50° C. and into the concentrated mass hexane was added further reaction mixture was heated to 45-50° C. for 30-45 min to get clear solution. Reaction mixture was slowly cooled to room temperature and stirred for 30 min. Stirred the precipitated mass for 30-45 min and filtered and washed the solid mass with hexane (10 ml). Dried the solid under vacuum at 40-45° C. Dry wt. 2.5 gm Yield=72.46%

Example 2

Purification of Crude Efinaconazole

Dissolved 40.0 gm of crude Efinaconazole in 120 ml of methanol at a temp of 30° C. and added 4.0 gm of activated carbon followed by stirred the mixture for 30-45 min. Filtered this solution to remove insoluble. 90 ml of water added to above filtrate and seeded reaction mass with 0.01 gm of efinaconazole then stirred the mixture for 60-20 min. and filtered the solid. Washed solid with 30 ml methanol and 20 ml of water and dried under vacuum at 45° C. to get 32 gm of pure crystalline Efinaconazole.

Yield=89%

The invention claimed is:

1. An improved process for the preparation of Efinaconazole or pharmaceutically acceptable salts thereof comprises reacting (2R,3S)-2-(2,4-difluorophenyl)-3-methyl-2-[(1H-1,2,4-triazol-1-yl)methyl]oxirane with 4-methylenepiperidine or its acid addition salt in the presence of an alkali or an alkaline earth metal halide.

2. The process according to claim 1, wherein an alkali or an alkaline earth metal halide is selected from lithium halide, sodium halide, potassium halide, rubidium halide, cesium halide, beryllium halide, magnesium halide, calcium halide, strontium halide and barium halide.

3. The process according to claim 2, wherein an alkali or an alkaline earth metal halide is lithium halide.

* * * * *